US010007920B2

(12) United States Patent
Ranieri et al.

(10) Patent No.: US 10,007,920 B2
(45) Date of Patent: Jun. 26, 2018

(54) DEVICE AND METHOD FOR DETECTION OF COUNTERFEIT PHARMACEUTICALS AND/OR DRUG PACKAGING

(71) Applicant: The United States of America, as represented by the Secretary, Department of Health & Human Services, Washington, DC (US)

(72) Inventors: Nicola Ranieri, Mainville, OH (US); Mark R. Witkowski, West Chester, OH (US); Mike D. Green, Atlanta, GA (US)

(73) Assignee: The United States of America, as represented by the Secretary, Department of Health and Human Services, Washington, DC (US)

( * ) Notice: Subject to any disclaimer, the term of this patent is extended or adjusted under 35 U.S.C. 154(b) by 66 days.

(21) Appl. No.: 14/650,244

(22) PCT Filed: Dec. 6, 2013

(86) PCT No.: PCT/US2013/073526
§ 371 (c)(1),
(2) Date: Jun. 5, 2015

(87) PCT Pub. No.: WO2014/089406
PCT Pub. Date: Jun. 12, 2014

(65) Prior Publication Data
US 2015/0310454 A1     Oct. 29, 2015

Related U.S. Application Data

(60) Provisional application No. 61/734,829, filed on Dec. 7, 2012.

(51) Int. Cl.
G01N 21/958     (2006.01)
G06Q 30/00      (2012.01)
(Continued)

(52) U.S. Cl.
CPC ..... *G06Q 30/0185* (2013.01); *G01N 21/9508* (2013.01); *G01N 33/15* (2013.01);
(Continued)

(58) Field of Classification Search
CPC ........ G06Q 30/00; G06Q 50/22; G01N 21/00; G01N 21/95; G01N 21/9508; G01N 33/15;
(Continued)

(56) References Cited

U.S. PATENT DOCUMENTS 5,245,179 A     9/1993  Chang et al.
5,479,258 A    12/1995  Hinnrichs
(Continued)

FOREIGN PATENT DOCUMENTS

EP     0999440 A1     5/2000
EP     1688851        8/2006
(Continued)

OTHER PUBLICATIONS

International Search Report dated Mar. 9, 2014 for PCT/US2013/073526.
(Continued)

*Primary Examiner* — Dramos I Kalapodas
(74) *Attorney, Agent, or Firm* — Klarquist Sparkman, LLP

(57) ABSTRACT

One aspect of the invention provides a device for detecting a counterfeit product. The device includes: a plurality of light sources configured to emit light at a plurality of different wavelengths onto an object potentially including a suspect product; at least one image acquisition device adapted and configured to acquire image data; and a communications interface adapted and configured to transmit the image data to a computing device selected from the group consisting of: a tablet computer and a smartphone.

17 Claims, 15 Drawing Sheets

(51) Int. Cl.
    *G01N 33/15*     (2006.01)
    *G01N 21/95*     (2006.01)
    *G06K 9/20*     (2006.01)
    *G06Q 50/22*     (2018.01)
    *H04N 5/225*     (2006.01)

(52) U.S. Cl.
    CPC ........... *G06K 9/2018* (2013.01); *G06Q 50/22* (2013.01); *H04N 5/2256* (2013.01)

(58) Field of Classification Search
    CPC ........... G01N 21/27; G01N 2201/0627; G01N 21/33; G01N 21/3563; G01N 2201/0221; G01N 21/64; G06K 9/20; G06K 2019/0629; G06K 19/16; G06K 9/4652; G06K 9/00577; G06K 9/2018; G06K 2209/01; G06K 9/00; G06K 9/34; G06K 19/07749; G06K 19/06009; G01J 2005/0081; G01J 3/32; G01J 3/501; G01J 3/50; G01J 3/0272; G01J 3/10; G07D 7/128; G07D 7/0032; G03H 1/0011; G03H 2001/0016; G02B 5/18
    See application file for complete search history.

(56) References Cited

U.S. PATENT DOCUMENTS

| | | | |
|---|---|---|---|
| 6,535,637 B1 | 3/2003 | Wootton et al. | |
| 6,771,369 B2* | 8/2004 | Rzasa | G01J 3/02 250/339.07 |
| 6,853,447 B2* | 2/2005 | Goetz | B07C 5/342 356/237.1 |
| 7,528,957 B2* | 5/2009 | Lewis | G01J 3/02 356/419 |
| 7,656,520 B2 | 2/2010 | Cohn | |
| 8,052,058 B2* | 11/2011 | He | G06Q 10/06 235/462.09 |
| 8,186,874 B2* | 5/2012 | Sinbar | G01N 33/15 374/45 |
| 2001/0016059 A1 | 8/2001 | Krahn | |
| 2002/0012895 A1 | 1/2002 | Lehmann | |
| 2003/0117620 A1 | 6/2003 | Balas | |
| 2004/0021861 A1* | 2/2004 | Lewis | G01J 3/02 356/326 |
| 2004/0135086 A1* | 7/2004 | Lewis | G01N 1/06 250/339.12 |
| 2004/0207842 A1 | 10/2004 | Rzasa | |
| 2004/0208373 A1 | 10/2004 | Aoki | |
| 2005/0108044 A1 | 5/2005 | Koster | |
| 2005/0243305 A1 | 11/2005 | Vig et al. | |
| 2005/0259254 A1 | 11/2005 | Soller et al. | |
| 2005/0264813 A1 | 12/2005 | Giakos | |
| 2006/0062734 A1 | 3/2006 | Melker et al. | |
| 2007/0153512 A1 | 7/2007 | Hendrie | |
| 2007/0260487 A1* | 11/2007 | Bartfeld | G06F 19/3462 705/2 |
| 2007/0265880 A1* | 11/2007 | Bartfeld | G06F 19/3462 705/2 |
| 2008/0151112 A1 | 6/2008 | Basile et al. | |
| 2009/0002992 A1 | 1/2009 | Dallas et al. | |
| 2009/0023991 A1 | 1/2009 | Gono | |
| 2009/0232276 A1* | 9/2009 | Kogan | G01N 23/20 378/53 |
| 2010/0110308 A1 | 5/2010 | Nicholson et al. | |
| 2011/0280480 A1 | 11/2011 | Simske et al. | |
| 2011/0293166 A1 | 12/2011 | Sinbar et al. | |
| 2012/0012750 A1* | 1/2012 | Sinbar | G01N 33/15 250/339.03 |
| 2012/0013734 A1* | 1/2012 | Ranieri | G01J 3/02 348/125 |
| 2012/0098439 A1 | 4/2012 | Recker et al. | |
| 2014/0053586 A1* | 2/2014 | Poecher | G01D 1/18 62/126 |

FOREIGN PATENT DOCUMENTS

| | | |
|---|---|---|
| JP | 2008 282274 | 11/2008 |
| WO | WO 2000/67204 | 11/2000 |
| WO | WO 02/25568 A2 | 3/2002 |
| WO | WO 2003/060443 | 7/2003 |
| WO | WO 2005/040739 | 5/2005 |
| WO | WO 2006/086085 | 8/2006 |
| WO | WO 2010/120555 | 10/2010 |

OTHER PUBLICATIONS

Supplementary European Search Report for EP 13859839, dated Jun. 7, 2016.
International Preliminary Report on Patentability for PCT/US2013/073526, dated Jun. 9, 2015.
Examination Report issued by the European Patent Office dated Oct. 16, 2017, for related European Patent Application No. 13859839.6, 7 pages.

* cited by examiner

DEVICE AND METHOD FOR DETECTION OF COUNTERFEIT PHARMACEUTICALS AND/OR DRUG PACKAGING

This application claims priority to U.S. Provisional Application No. 61/734,829, filed Dec. 7, 2012, incorporated by reference in its entirety herein.

STATEMENT REGARDING GOVERNMENTAL SUPPORT

The present subject matter was made with U.S. government support. The U.S. government has certain rights in this subject matter.

FIELD OF INVENTION

The present invention generally relates to methods and devices for the detection of counterfeit pharmaceuticals and/or the packaging therefore and more particularly devices and method for detection of counterfeit pharmaceuticals and/or the packaging using visible and non-visible radiation and more particularly devices and method for in-situ detection of counterfeit pharmaceuticals using visible and non-visible radiation. Although a preferred use of the present invention is in the detection of counterfeit pharmaceuticals, it can also be used in a variety of other forensic and public health applications.

BACKGROUND OF THE INVENTION

The amount of counterfeit pharmaceuticals entering the United States continues to increase. Such counterfeit pharmaceuticals are illegally imported into the United States, and are commonly available over the Internet. It may be difficult to determine the authenticity of a pharmaceutical, since the genuine and counterfeit products may have nearly identical appearances and markings (e.g., shape, color, size, packaging, labeling, etc.), even when viewed by professionals. The detection of counterfeit pharmaceuticals is important, since the efficacy of a counterfeit product can be lower than the actual product. In addition, the counterfeit product may contain toxic components or other components that might result in side effects which are not associated with the real product. Also, such counterfeit products also result in severe monetary loss to pharmaceutical companies and retailers.

Current methods for detecting counterfeit pharmaceuticals include vibrational spectroscopy, x-ray diffraction, gas chromatography, liquid chromatography and mass spectrometry. These methods, although often effective, require expensive and bulky instrumentation, and are generally performed in a laboratory.

It thus would be desirable to provide a new device and methods for detecting counterfeit pharmaceuticals and/or packaging from the pharmaceuticals and/or packaging from an authorized manufacturer, supplier and the like. It would be particularly desirable to provide such devices and methods that would be portable and usable at any desired location such as the inspection point for customs. It also would be particularly desirable to provide such devices that would be hand-held and use visible and/or non-visible light to illuminate suspect pharmaceuticals and/or packaging and determining from such illumination if the pharmaceuticals and/or packaging being examined are counterfeit pharmaceuticals and/or packaging. Such detection devices preferably would be simple in construction and less costly than prior art devices and such methods would not require highly skilled users to utilize the device.

SUMMARY OF THE INVENTION

One aspect of the invention provides a device for detecting a counterfeit product. The device includes: a plurality of light sources configured to emit light at a plurality of different wavelengths onto an object potentially including a suspect product; at least one image acquisition device adapted and configured to acquire image data; and a communications interface adapted and configured to transmit the image data to a computing device selected from the group consisting of: a tablet computer and a smartphone.

This aspect of the invention can have a variety of embodiments. In some embodiments, the device does not include a display device. The communications interface can be a wireless interface. The communications interface can be a wired interface.

The device can further include a housing, wherein the plurality of light sources and the at least one image acquisition device are coupled to the housing so that the plurality of light sources and the at least one image acquisition device are maintained in fixed relation to each other while the object is being illuminated.

The device can further include a control device adapted and configured to control operation of the plurality of light sources and the at least one image acquisition device.

The device can include two image acquisition devices.

The device can include one or more filters adapted and configured to selectively condition light entering the at least one image acquisition device.

The at least one image acquisition device can include one or more CCD arrays.

At least one of the plurality of light sources can be configured so as to emit light having an infrared wavelength. At least one of the plurality of light sources can be configured so as to emit light having a visible wavelength. At least one of the plurality of light sources can be configured so as to emit light having an ultraviolet wavelength.

The light sources can be LED light sources. The light sources can be tungsten light sources.

Another aspect of the invention provides a method for detecting a counterfeit product, comprising the steps of: providing a device as described herein; establishing a communications link with a tablet computer or a smartphone; using the device to image one or more products; and using the tablet computer or smartphone to view or analyze images or data from the device.

BRIEF DESCRIPTION OF THE DRAWING

For a fuller understanding of the nature and desired objects of the present invention, reference is made to the following detailed description taken in conjunction with the accompanying drawing figures wherein like reference character denote corresponding parts throughout the several views and wherein.

DESCRIPTION OF THE PREFERRED EMBODIMENT

Figure 1:
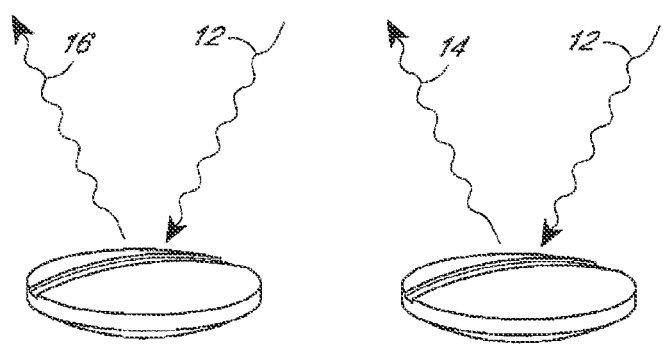
FIG. 1 is a schematic diagram illustrating the basic principle used in some advantageous embodiments of the invention.

The present invention in its broadest aspects includes devices and methods for the detection of suspected counterfeit pharmaceuticals including the packaging thereof. Such methods include exposing an authentic pharmaceutical and a corresponding suspected counterfeit pharmaceutical to one or more light sources having selected wavelengths and visually detecting a difference in color, brightness, contrast, darkening and/or other visual effect(s) between the authentic and suspected counterfeit pharmaceuticals. The device, embodying such methods, includes a plurality of light sources that generate the light to which the authentic and suspected counterfeit pharmaceuticals are exposed. In further embodiments, such light is generated using a hand-held, portable device and one or more LED (light emitting diode) comprise the one or more of the plurality of light sources.

As indicated above, the suspected counterfeit is visually observed when exposed to the light from the one or more light sources to determine if there is a difference in color and/or other visual effect(s), such as brightness, contrast, darkening, between an authentic pharmaceutical/packaging and the suspected counterfeit. Such differences occur because the light characteristics (e.g., light reflection, light absorption and fluorescence) are dependent upon the composition and makeup of the pharmaceutical and/or packaging. In other words, a difference in the composition or formulation between a counterfeit pharmaceutical and that for an authentic pharmaceutical can be revealed as a change in color and/or other visual effect(s) such as brightness, contrast, darkening, particularly when the two are exposed to different wavelengths of light and/or radiation. Similarly, differences in the materials used in the packaging components between the counterfeit and authentic packaging also should be visually observed when the two are exposed to different wavelengths of light/radiation.

It has been found that differences in color and/or other visual effect(s) such as brightness, contrast, darkening, are observable when authentic and counterfeit pharmaceutical products and/or product packaging are illuminated with appropriate wavelengths of light, and also when being observed through appropriate filters. Without being bound by any particular theory, it is believed that these differences in color and/or other visual effect(s) such as brightness, contrast, darkening, are produced by slight differences in the fluorescent response of the excipients (or other components) within the pharmaceutical product (e.g., tablet or capsule), in the inks on the products, or in the product packaging itself. It has also been noted that lot-to-lot variability in authentic pharmaceutical products in these properties are minimal since the production processes of such products are highly controlled. Thus, the appearance of different lots of such authentic pharmaceuticals will be very similar when viewed under different wavelengths of light. In contrast, suspect counterfeit products do not have a single source, are not controlled as highly in the various sources, and consequently have a greater variability in appearance and will generally appear different from authentic products and packaging. For example, a counterfeiter may use an ink or dye that has a different composition than the originator. Although this different ink or dye composition may appear to have the same color to the naked eye, the different composition may fluoresce differently.

Referring now to the various figures of the drawing wherein like reference characters refer to like parts, a schematic diagram illustrating the basic principle used in advantageous embodiments of the invention is shown in FIG. 1. As schematically illustrated, the incident light 12 impinges upon both a counterfeit and authentic pharmaceutical product (depicted in the figure as a tablet).

The intensity and wavelengths of the reflected light 14, 16 differs between the two products, resulting in an observable difference in color and/or other visual effect(s) between the two products and/or the product packaging. This observable difference occurs upon illumination with light of one or more particular wavelengths, which results in an observable difference in color and/or other visual effect(s). Also, differences that are not detectable by visually inspecting a pharmaceutical product with the naked eye under ambient lighting conditions are detected using the device and methods described herein. This principle is utilized in embodiments of the invention to produce an inexpensive and portable devices and screening methods for determining whether a pharmaceutical product of unknown origin is legitimate or not.

Counterfeit Pharmaceutical Detection Devices

Figure 2A:
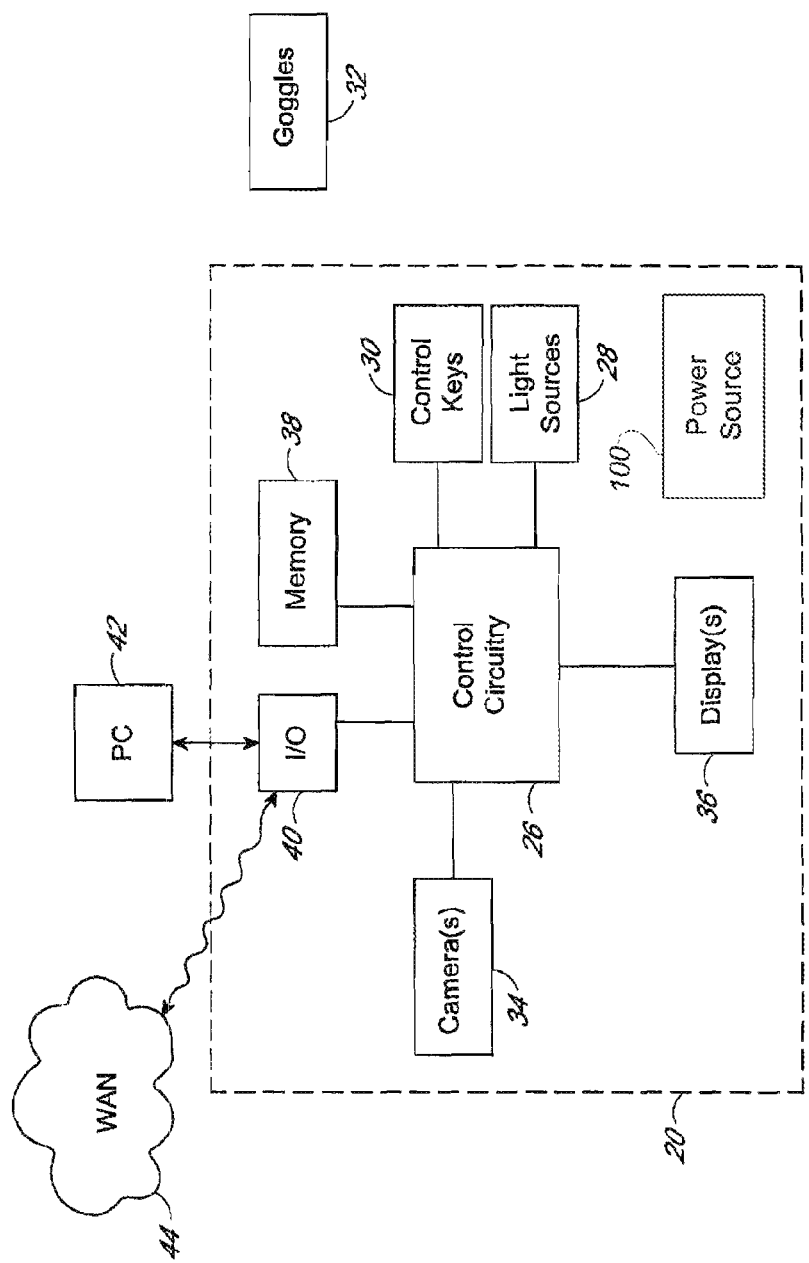
FIG. 2A is a schematic diagram of an embodiment of a counterfeit drug-detecting LED device of the present invention, including external applications.

Referring now to FIG. 2A, there is shown one embodiment of a counterfeit pharmaceutical detection device 20 according to the present invention. Such a device 20 includes control circuitry 26 that is composed of circuit components or elements that can carry out the functions described herein and/or such components along with a controller (e.g., a microprocessor, microcontroller, application specific integrated circuit (ASIC) or the like) or a controller. Such control circuitry 26 is configured and arranged so as to control the functionalities of the detection device including the light sources 28, display(s) 36 and the image acquisition device(s) such as a camera(s) 34.

In illustrative embodiments, such a device 200 also includes a plurality of switches, buttons, or control keys 30 that are operably coupled to the control circuitry 26 that are used by the user for turning on or off one of more light sources 28. The switches, buttons, or control keys 30 can be implemented as physical hardware components and/or software elements (e.g., widgets displayed on a graphical user interface). Alternatively, the detection device 20 embodies any of a number of other devices or techniques as is known to those skilled in the art that can control the selection of the one or more light sources. In an illustrative embodiment, the detection device display 36 is configured so as to emulate a touch screen having for example one or buttons displayed thereon each being representative of a light source. Thus, when a user touches one of the displayed buttons the control circuitry causes the corresponding light source to be turned on/off. In yet another embodiment, a touch pad is provided that controls a cursor depicted on the screen. By moving the cursor to one of the buttons depicted on the screen and actuating the touch pad, the user can cause a given light source to be turned on/off.

In yet further embodiments, the control circuitry 26 is configured so that when a user provides an input indicating that the detection device is appropriately positioned with respect to the suspect product, the control circuitry includes instructions and criteria that controls the selection of the light sources, the turning of the light sources on/off as well as the sequence and which light sources to turn on/off, and the acquisition of image data using the appropriate image acquisition devices.

As described herein, the light sources are configured and arranged so as to have particular wavelengths that are used for the illumination of a pharmaceutical product and/or product packaging. As described herein, the illumination of the pharmaceutical products under specific wavelengths can produce a detectable difference in appearance (e.g., color and/or brightness) between a legitimate or authentic pharmaceutical product and a counterfeit pharmaceutical product. Thus, the light sources selected for use in illuminating at least the suspect product is done so as to use light sources having wavelengths that are likely to produce a detectable difference in appearance (e.g., color and/or brightness) between a legitimate or authentic pharmaceutical product and a counterfeit pharmaceutical product.

In some cases, the pharmaceutical product(s) are viewed by a user under the desired illumination (e.g., wavelength) through a filter, which can be incorporated into glasses or goggles 32 which filter out illumination wavelengths, and allow the wavelengths of the light or radiation returning from the illuminated product(s) to pass through. Although the different appearances of different products are not generally predictable a priori, with some experimentation, it has been found relatively easy to determine and document which illumination and filter wavelengths work well for distinguishing a given pharmaceutical product from a counterfeit version of that product.

Thus, it is within the scope of the present invention to establish criterion and operating protocols to follow that allow one to determine the type of light, the color of such light and any filtering requirements for viewing a suspect product to see if it is an authentic product. For example, it may be established from a series of experiments that, to determine whether an unknown tablet purportedly from Manufacturer A is counterfeit, the suspect product should be viewed under green light with a yellow filter, and in addition that when viewed in this manner, the color of the legitimate product has a bright yellow hue. Thus, when a suspect product when viewed under such conditions is a darker brownish and slightly red appearance, one can conclude that the suspect product is a counterfeit.

In yet further embodiments and for purposes of making the viewing more convenient and to potentially expand the observable emission spectrum, the detection device 20 further includes one or more image acquisition devices (e.g., cameras, CCD, night vision devices) 34 that are usable for imaging the pharmaceutical products under the desired illumination. In more particular embodiments, such image acquisition devices 34 are capable of detecting the light returning from the illuminated product or object and to provide an output representative of the detected light. For example, in a particular embodiment, an image acquisition device 34 is configured and arranged so it detects light at or about a predetermined wavelength corresponding to a given color of light and provides an output representative of the detected brightness of the light.

In some embodiments, the one or more image acquisition devices 34 are capable of simultaneously imaging in a plurality of spectrums such as UV, visible light, and infrared. These images can also be transmitted and/or displayed simultaneously using the components discussed below.

As described herein, such image acquisition devices 34 are further configurable with a filter or the like so the returning light is filtered so that the light impinging upon the sensing component(s) of the image acquisition device 34 is at or about the given wavelength. In illustrative embodiments, such image acquisition devices 34 comprise any of a number of devices that are known to those skilled in the art including, but not limited to a CCD camera or the like.

As indicated herein, the light illuminating the suspect product and the authentic product includes non-visible radiation or light such as light in the UV and IR ranges that are outside the human visual spectrum. In such cases, the image acquisition device includes a device (e.g., night vision devices) that are sensitive to light or radiation having such wavelengths. This expands the range of light usable for illuminating the suspect and authentic product and thus expands the range over which differences in appearance can be exploited.

In yet further embodiments, the image acquisition device 34 is configured so as to include an optical adjustment capability, such that the image acquisition device is usable as a "portable microscope" by using macro zoom capabilities of the incorporated lens(es). A hand held up-close viewing of the objects being illuminated while using such macro lens, allows for high resolution viewing.

In further embodiments such a detection device 20 includes a display 36 (e.g., LCD display) that is operably coupled to the control circuitry 26. In this way, when image data is acquired by a given image acquisition device, the control circuitry provides outputs to the display so as to thereby cause the display to provide an image having a color and brightness that is representative of the image data acquired or sensed by the given acquisition device. It also is within the scope of the present invention for the control circuitry 26 to combine image data from one or more image acquisition devices so that the display reproduces a color image representative of the color that would be observed as if it were being viewed by the eye. In sum, the display is usable for visually displaying images of the pharmaceutical product(s) under the selected wavelength(s).

The detection device also is configurable with a memory 38 such as a memory (e.g., non-volatile or FLASH memory, an optical drive, or a solid state drive) to store information for the operation of the detection device, image data representative of one or more authentic pharmaceutical products or packaging. In more particular embodiments, such information includes instructions regarding the appropriate wavelengths to use for various products and previously acquired images of authentic and counterfeit pharmaceutical products. Such information is intended to allow an agent in the field or in situ to easily compare the appearance of suspected counterfeit to the authentic product.

For example, an image of an authentic product is stored in the memory 38 which is retrieved from the memory by the control circuitry 26. The image data is sent to the display 34 so that the user can use the stored image as a reference image for comparison with the acquired image of the suspect product. The control circuitry 26 is configurable so that the stored image is displayed at least one of before or after the image of the suspect product is acquired. In further embodiments, the control circuitry 26 is configured so that both the stored image and the acquired image are displayed at the same time (e.g., side by side arrangement) much as would be seen if the detection device was illuminating the authentic and suspect products at the same time.

In yet further embodiments, the detection device 20 includes one or more communication devices or input/output devices 40 that allows communication between an external device such as for example a computer (e.g., personal computer) and the detection device. In this way, instructions, image data of authentic products or application program data/instructions can be downloaded to the detection device or previously acquired image data by others using such a device 20 either in a laboratory test environment or in the field can be downloaded to or from the detection device. Such an I/O device 40 includes a USB port or communication device, a network I/O device that allows communications over a wide area network (WAN) or a local area network (LAN) either using wireless or wired communication techniques, and/or a cellular transceiver adapted and configured to send and receive data over a cellular network (e.g., a network implanting the 3G or 4G standards).

Such a detection device 20 also includes a power source 100 that is operably coupled to the functionalities of the detection device and under the control of the control circuitry 26. Such a power source is any of a number of sources of electrical power as is known to those skilled in the art and including for example rechargeable or non-rechargeable batteries (e.g., alkaline, lithium ion, metal hydride and the like) and capacitors or high power capacitors. Such power sources 100 also can further include any of a number of electrical functionalities known to those skilled in the art (e.g., transformers) so as to control the power (voltage, current) being outputted by the power source so as to be at or about an appropriate value. In more particular embodiments, the detection device 20 is constructed so as to made in a hand-held form and be portable. In further illustrative embodiments, the power source is a battery such as a 12VDC portable battery, or is any center polarity power adapter (e.g., 12-15 VDC).

Figure 2B:
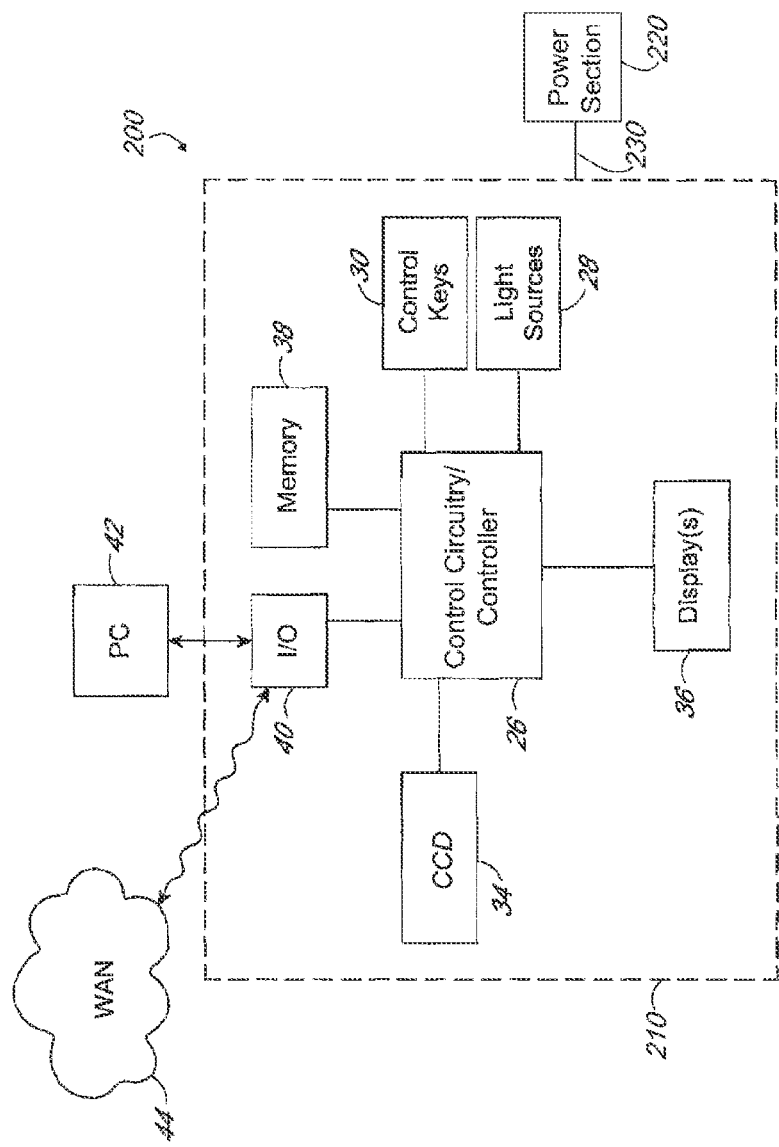
FIG. 2B is a schematic diagram of another embodiment of a counterfeit drug-detecting LED device of the present invention, including external applications.

Referring now to FIG. 2B there is shown a detection device 200 according to another embodiment of the present invention. Reference shall be made to the discussion above regarding FIG. 2A for details of devices or functionalities having common reference numerals. In this embodiment, the detection device 200 includes two sections, a scanning section 210 and a power section 220 that includes a power source 100. The power section 220 is operably coupled to the scanning section 210 by a cable 230 so that the power source supplies the power to operate the scanning section. In this arrangement, the scanning section 210 is configured and constructed so as to be made in a hand-held form and be portable. Such a power section 220 need not be configured or made so as to be hand-held but can be configured so as to be portable or fixed so as to provide a larger power source. For example, in an illustrative embodiment, the power section 210 is belt mounted so as to be worn about the waist of the user.

The devices and methods described herein are particularly well suited for field work, such as that done by Customs agents at airports, inspection stations and other ports of entry into the United States. In particular, this is the case as the detection device 20 or scanning section 210 are configurable so as to be made in a hand-held form and portable.

Figure 3A:
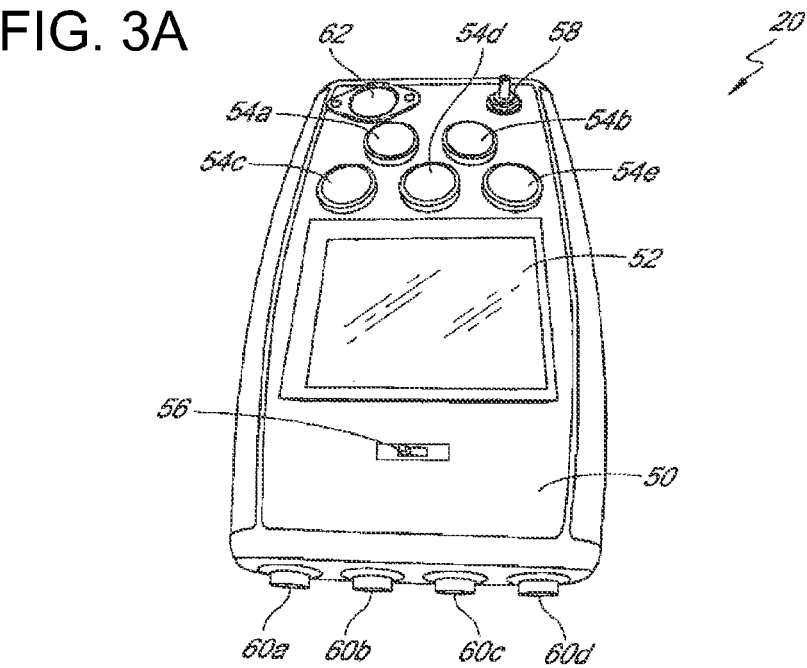
FIG. 3A is a top view of one embodiment of the counterfeit drug-detecting LED device of the present invention.

Referring now to FIG. 3A, B there is shown a representative example of a hand-held detection device according to the present invention. It should be recognized that is well within the skill of those knowledgeable in the art to configure the detection device as described in any of the embodiments described herein as well as configuring a scanning section 210 so as to embody feature shown and described herein in connection with FIGS. 3A-B.

There is shown in FIG. 3A, a top view of the detection device 20, which further includes a housing 50 in which various components of the device are disposed. One such component is an LCD display screen 52, which display allows the user to view images acquired by cameras 70*a*, 70*b* or other image acquisition devices described further below. Although the display will be described herein as producing a visible spectrum output, it will be appreciated that other image processing techniques can be used to provide a visible depiction or display of non-visible UV and/or IR wavelengths emitted by the product under view that are detectable only by the camera, whereby detectable differences can be found outside normal human vision capabilities. Depending on the product, this can enhance the differences seen between a legitimate and counterfeit product when viewed on the LCD display.

Figure 3B:
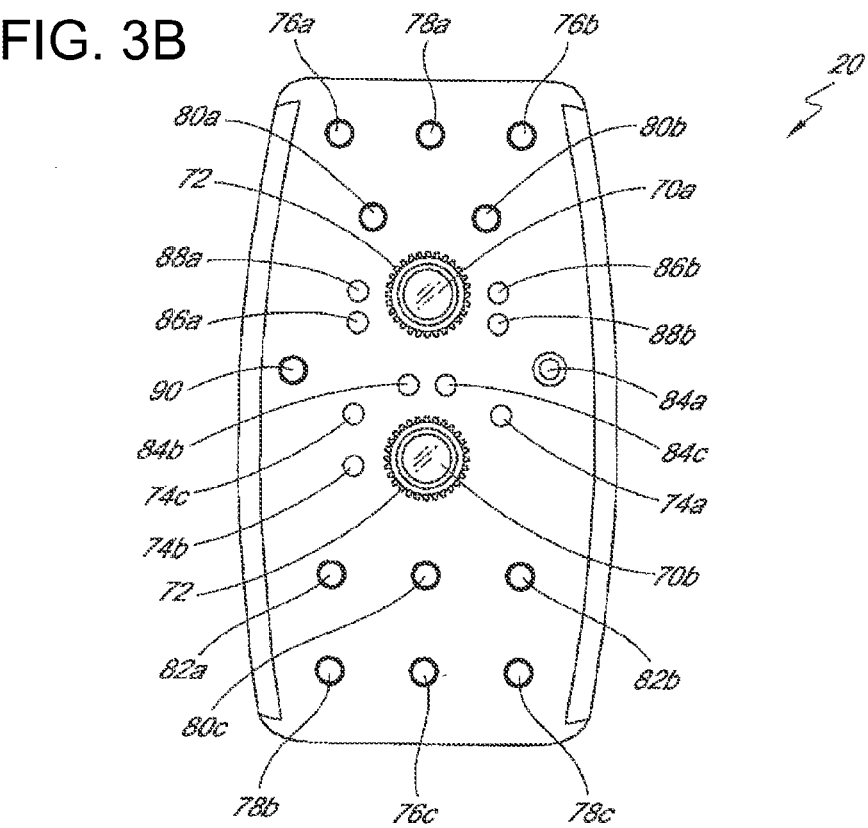
FIG. 3B is a bottom view of one embodiment of the counterfeit drug-detecting LED device of the present invention.

Also disposed on and/or within the housing are ultraviolet, infrared and white light momentary push buttons 54*a-e* which turn on and off certain light sources on the bottom of the housing (discussed in reference to FIG. 3B below) corresponding to the buttons. The housing also includes an on-off switch 56 and an illumination intensity control 58 which is connected to a subset of, or possibly all of, the light sources. UV-Visible momentary push-buttons 60*a-d* turn on and off certain light sources on the bottom of the housing (FIG. 3B).

Video output 62 interfaces with USB and power supply connections. Image capture or video capture may occur through the USB connection. In the device shown in FIG. 3A, button 54*a* controls a white light source used for normal light illumination, and buttons 54*b-e* control LEDs having center wavelengths of about 351 nm, about 800 nm, about 900 nm, and about 1050 nm, respectively. It will be appreciated that the such light sources are not pure, but emit in a wavelength band centered at or near the recited center wavelength. The bandwidth is not particularly critical to device function. It should be recognized that LED light sources with the recited center wavelengths and having suitable bandwidths are commercially available.

A "white" light source can contain a set of narrowband emissions at different locations in the visible spectrum or can have a flatter broadband emission spectrum across most or all of the visible range.

In addition, referring to FIG. 3A, UV-Visible momentary push buttons 12*a-d* control light sources having center wavelengths of about 525 nm, about 470 nm, about 455 nm, and about 405 nm, respectively. An illumination intensity control 58 may be provided to provide intensity adjustability for low or highly reflective surfaces.

Referring to FIG. 3B, the bottom of the housing includes two high sensitivity CCD chips (cameras) 70a and 70b, either or both of which may contain a removable color lens filter, which, in one embodiment, is held in place by a rubber grommet 72. Although CCD chips are exemplified herein, the device can comprise any light sensitive device as are know to those skilled in the art such as photodiodes or the like. In further embodiments, the camera lenses are dismountable, high quality precision ground, multi-element glass micro-board lenses which results in chromatic aberration reduction. The device 20 is usable with one or both color filters in place, or is usable without filters. As indicate herein, in some embodiments, the device does not comprise a display or an image acquisition device (e.g., CCD chip).

In more particular exemplary embodiments, the arrangement of the LEDs in FIG. 3B is as follows: 351 nm (74a-c), 405 nm (76a-c), 455 nm (78a-c), 470 nm (80a-c), 525 nm (82a-b), 800 nm (84a-c), 900 nm (86a-b), 1050 nm (88a-b) and white light (90). The 351 nm LEDs are generally of lower output power than the 405-800 nm LEDs. The 900 nm and 1050 nm LEDs emit light in the infrared region, while the 351 nm LEDs emit light in the ultraviolet region. These wavelengths are illustrative of a particular exemplary embodiment. Thus, it is within the scope of the present invention to utilize other wavelengths and/or wavelength combinations that are more appropriate for scanning and evaluating particular pharmaceutical and/or packaging or packaging components.

The detection device 20 including the control circuitry is configurable so as to provide simultaneous multiple light source illumination capability for various specific analysis requirements. It will be appreciated that the arrangement of buttons/controls shown in FIG. 3A, and LEDs shown in FIG. 3B, are exemplary, and many variations of these can occur and are within the scope of the present invention. In addition, the invention also is not limited to the particular wavelengths mentioned above. Many variations of these can be used, and are also within the scope of the present invention.

The detection device 20 described herein is ergonomically designed for hand-held comfort, is portable and lightweight, and fits inside a shirt or jacket pocket. Thus, it is well suited for work in the field, and obviates the need to send field samples to a laboratory for analysis. Thus, customs agents can quickly determine whether a suspect pharmaceutical is in fact counterfeit. If desired, the suspected counterfeit pharmaceutical can be subjected to further confirmatory testing using conventional methods.

Methods of Detecting Counterfeit Pharmaceutical Products

Figure 4:
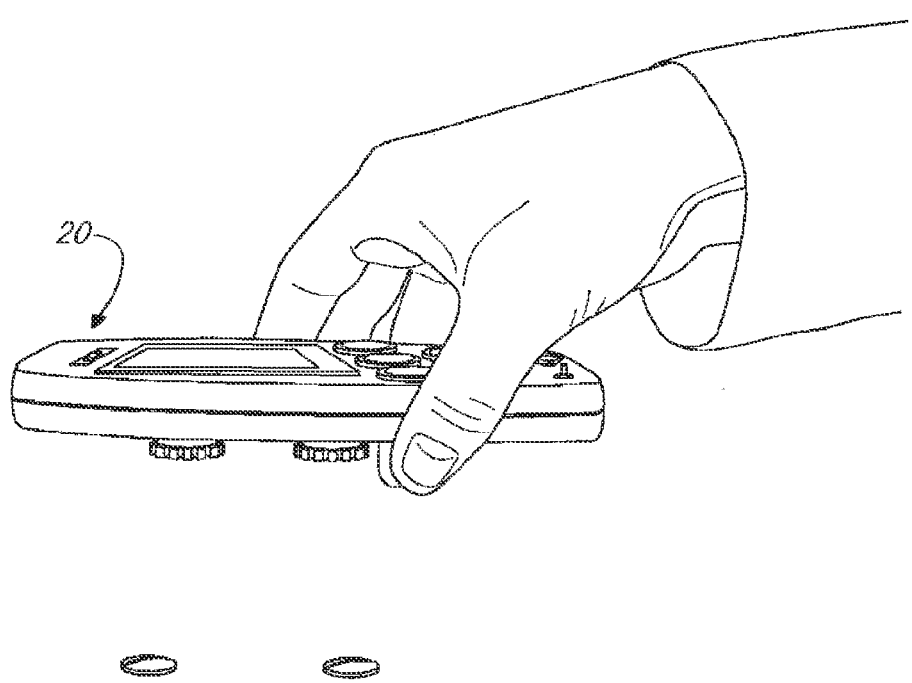
FIG. 4 is a diagram of the counterfeit drug-detecting LED device in use with two tablets.
Figure 5:
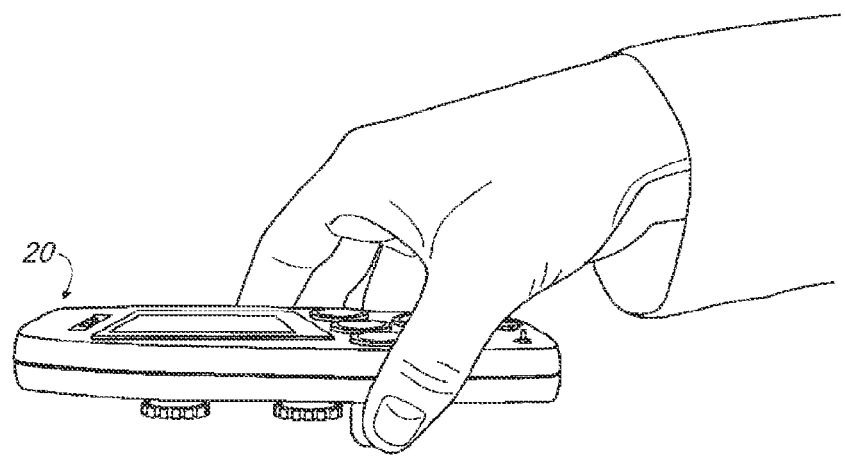
FIG. 5 is a diagram of the counterfeit drug-detecting LED device in use with tablets in their packaging.
Figure 5:
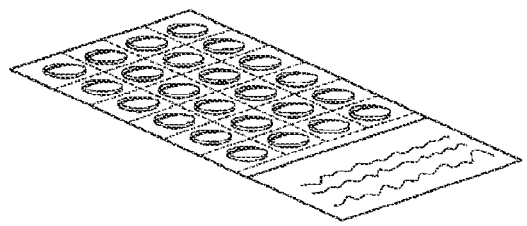
Figure 6:
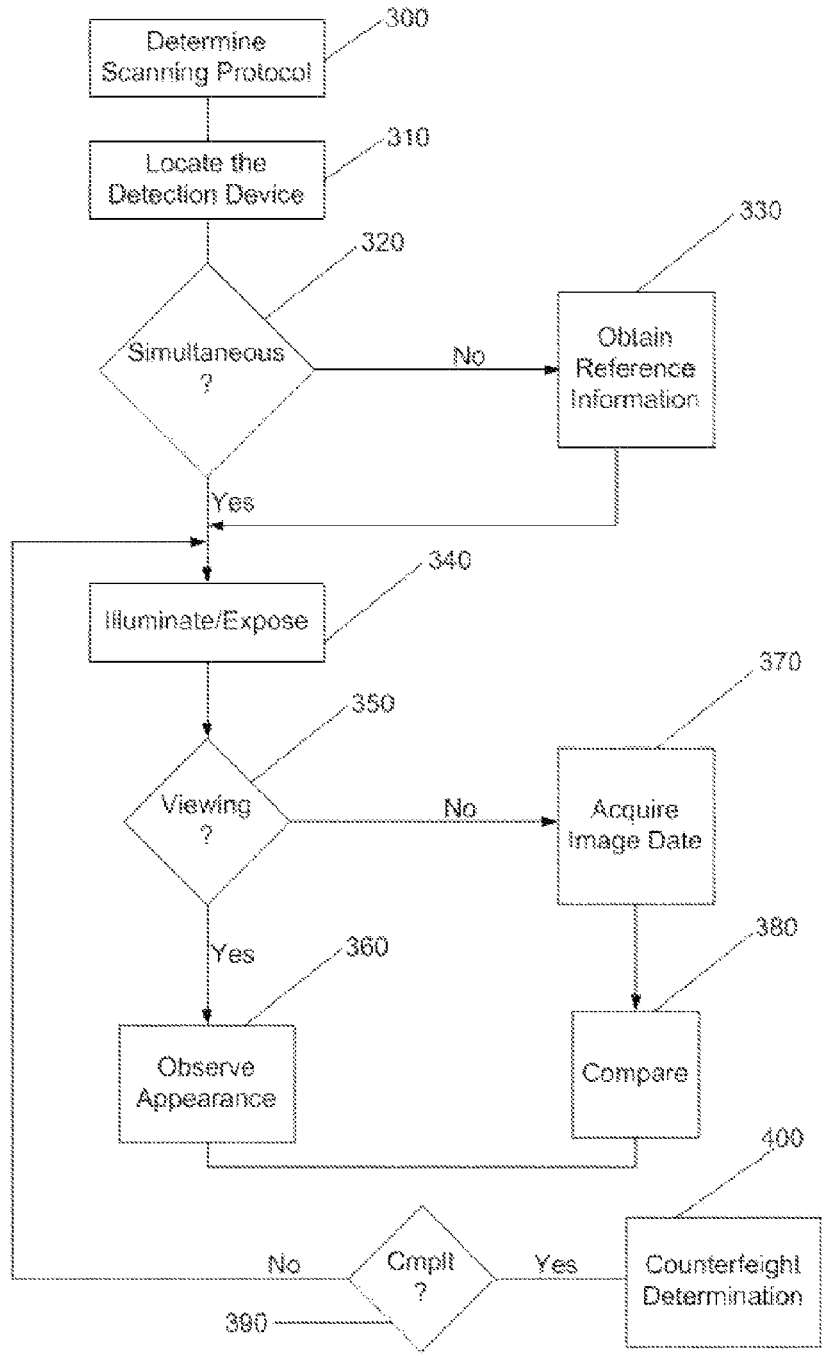
FIG. 6 is a high level flow diagram illustrating an embodiment of the methodology of the present invention.
Figure 7:
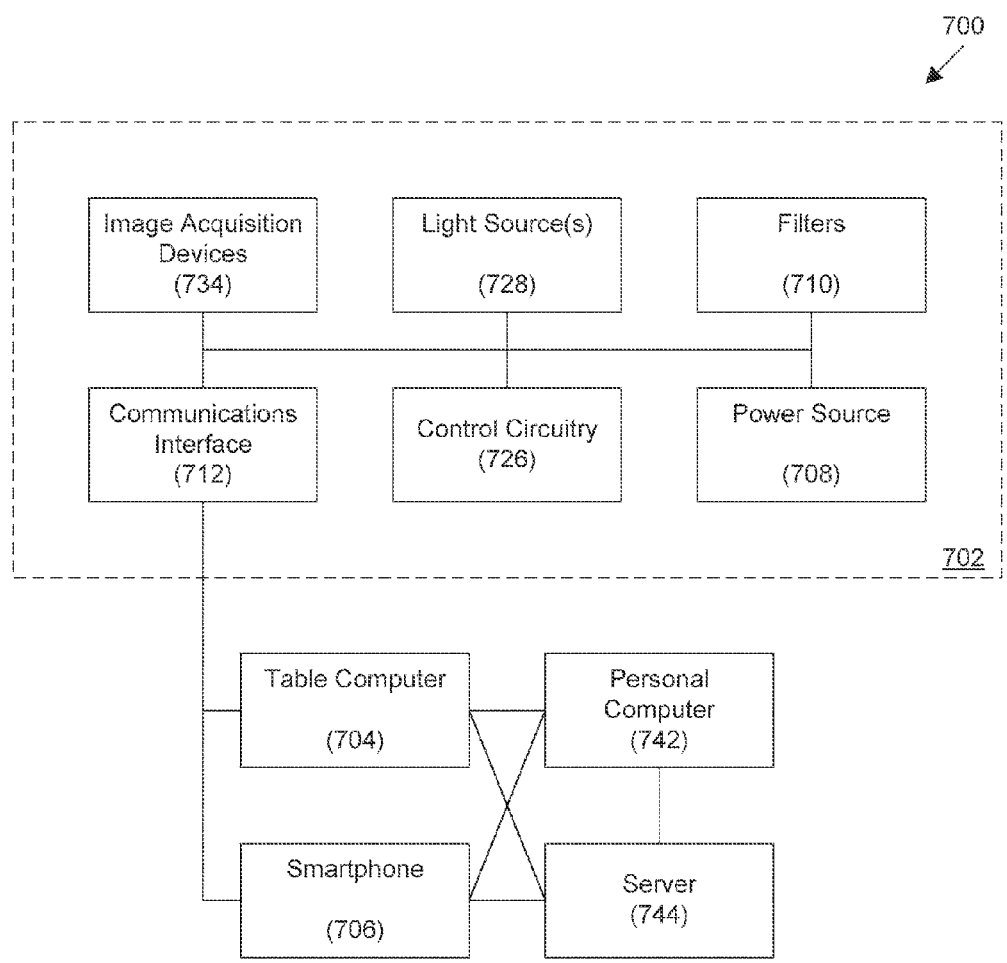
FIG. 7 depicts a combined hand-held device and tablet/smartphone platform according to an embodiment of the present invention.

Now referring to FIGS. 4 and 5 which are diagrams showing the device in use for detection of suspected counterfeit pharmaceutical products both out of (FIG. 4) and in (FIG. 5) the packaging material and also to FIG. 6, which is a high level flow diagram of an illustrative embodiment of the methodology of the present invention. When a user is to conduct an examination of a suspect product or packaging, the user undertakes the steps necessary to establish the scanning protocol that will be used to determine if the suspect product is an authentic product or a counterfeit, Step 300. The user initially determines the light sources having the wavelengths of light that should be used during such scanning so as to create the potential for determining from such a light scanning process if the suspect product is authentic or not. In addition, the user determines if the light returning from the illuminated object(s) should be filtered or appropriately treated in conjunction with a direct viewing by the user or viewing via an image acquisition device. As provided herein, in an embodiment of the present invention the suspect product or the suspect product and authentic product are viewed at the same time by a user that is wearing colored goggles or glasses.

If image acquisition devices are being utilized to acquire image data representative of the returning light (color and/or brightness) the user determines which of such devices should be used and in combination with what illuminating light sources. In an embodiment of the present invention, the user can operate a filter wheel to position a desired filter (e.g., colored filters such as orange or yellow, polarized, UV cutoff, and the like) over one or both camera lenses comprising the image acquisition devices. Thus, the user determines the appropriate filtering. It should be noted that the device may contain no camera or display, a single camera, two cameras, or three or more cameras, and that the presence of two cameras is only exemplary.

Also, the user can determine if the detection device should be oriented so as to be at an angle with respect to the object(s) being illuminated. For example, holding the detection device at oblique angles in some cases allow for better imaging/scanning analysis.

In sum, the user determines at the outset the light sources, the light illumination sequencing, the image acquisition devices and other control parameters and the like that should be utilized to scan the suspect product/packaging and taking the appropriate steps so that scanning is done according to the determined protocol.

After establishing the protocol and setting up the detection device, the user locates the detection device in proximity to the suspect product, and in the case where the protocol includes simultaneously scanning the suspect and authentic product, locates the device in proximity to both of them, Step 310. For example and as shown in FIGS. 4-5, the detection device 20 is held above the suspected counterfeit pharmaceutical product (FIG. 4) and/or product packaging (FIG. 5) by the user. In addition, the user can orient the detection device with respect to the object(s) to be illuminated in cases where better imaging and the like would be achievable.

If it is next determined if the process is proceeding with simultaneously viewing of the suspect and authentic product or not, Step 320. In the case where a suspected counterfeit pharmaceutical product and the corresponding authentic product (and/or product packaging) are placed side by side (Yes, Step 320), the suspect product and the authentic product are illuminated with the detection device 20 using one or more wavelengths of visible, ultraviolet or white light, Step 340 and differences in color and/or brightness of the authentic and suspected pharmaceutical products are observed or viewed by the user, Step 350. In an illustrative exemplary embodiment, the authentic and suspected pharmaceutical products and/or packaging are viewed under white light and light having a specific wavelength (e.g., 405, 455, 470 or 525 nm). As indicated herein, such viewing can be achieved by the user directly viewing the authentic and suspected pharmaceutical products and/or packaging while they are being illuminated and observing the appearance of both as they are being simultaneously illuminated. Alternatively, the appearance of the authentic and suspected pharmaceutical products and/or packaging are observed by viewing the appropriate LCD display screen 36.

The images of the two samples under the two different lighting conditions are then compared or the appearances of the samples are then compared, Step 360. Thereafter a determination is made whether or not the scanning protocol is completed, Step 390. If the process is not complete (No, Step 390), the process proceeds to illuminating or exposing at another set of wavelengths according to the protocol and steps 350 and 360 repeated as many times until it is determined that the process is complete (Yes, Step 390). If the process is determine to be complete, and if differences were observed from observing the appearance of the samples; such differences are evaluated to determine if they are representative of a suspected counterfeit, Step 400.

On the other hand, if it is next determined that the process is not proceeding with simultaneously viewing of the suspect and authentic product (No, Step 320), then the process proceeds with acquiring reference information that is representative of the authentic product, Step 330. For example, the control circuitry 26 retrieves information (acquired image data for the authentic product) from the memory 38 so it can be utilized later in the process. In this embodiment, the suspected counterfeit product is viewed alone, thus the suspected counterfeit product is illuminated with the detection device 20 using one or more wavelengths of visible, ultraviolet or white light, Step 340 and image data is acquired using the image acquisition devices, Step 370.

Thereafter, the acquired image data or image is then compared to the retrieved pre-existing image of the corresponding authentic product under the same illumination and detection conditions, Step 380. In this way, an agent in the field need not carry authentic samples of pharmaceutical products and or packaging with them as well as avoiding the need to take appropriate steps to maintain the authentic products so that they do not degrade, break down or otherwise become unusable as a reference sample.

In further embodiments the user would refer to the reference image one of before or after acquisition of the image for the suspect product and perform a comparison of the acquired image for the suspect product with reference image that was viewed before or after. In yet another embodiment and as provided herein, the control circuitry 26 controls the operation of the display 36 so that the reference image and the acquired image of the suspect product are viewed simultaneously by the user. In other words, the two images are compared or the appearances of the images are compared.

Thereafter a determination is made whether or not the scanning protocol is completed, Step 390. If the process is not complete (No, Step 390), the process proceeds to illuminating or exposing the suspect product to another set of wavelengths according to the protocol and Steps 340, 370 and 380 are repeated as many times until it is determined that the process is complete (Yes, Step 390). If the process is determine to be complete, and if differences were observed from the performed comparison; such differences are evaluated to determine if they are representative of a suspected counterfeit, Step 400.

Although a preferred embodiment of the invention has been described using specific terms, such description is for illustrative purposes only, and it is to be understood that changes and variations may be made without departing from the spirit or scope of the following claims.

Combined Hand-Held Device and Tablet/Smartphone Platforms

Referring now to FIG. 6, another aspect of the invention provides a platform 700 that leverages existing tablet computers or smartphones in order to provide a more robust detection platform while at the same time, reducing the cost and form factor of the detection device.

Platform 700 includes a detection device 702 and a tablet computer 704 and/or a smartphone 706.

Detection device 702 can include many or all of the components included in the devices depicted and discussed in the context of FIGS. 2A-3B. For example, the detection device 702 can include a power source 708, control circuitry 726, one or more light sources 728, one or more image acquisition devices 734, one or more filters 710, and/or a communications interface 712.

Tablet computer 704 is a mobile computer operated primarily through a touch screen. Advantageously, table computer 704 can be a commercially-available tablet computer 704 that is loaded with one or more software applications. For example, tablet computers of various sizes and features are available under the IPAD® trademark from Apple Inc. of Cupertino, Calif. and the KINDLE® trademark from Amazon Technologies, LLC of Reno, Nev. Additionally, various manufacturers produce tablets that utilize WINDOWS® operating systems available from Microsoft Corporation of Redmond, Wash. or ANDROID™ operating systems available from Google Inc. of Mountain View, Calif.

Smartphone 706 is a mobile telephone that implements a mobile operating system to provide computing capabilities. Advantageously, smartphone 706 can be a commercially-available smartphone 706 that is loaded with one or more applications. For example, smartphones of various sizes and features are available under the IPHONE® trademark from Apple Inc. of Cupertino, Calif. Additionally, various manufacturers produce smartphones that utilize WINDOWS® operating systems available from Microsoft Corporation of Redmond, Wash. or ANDROID™ operating systems available from Google Inc. of Mountain View, Calif.

Communications interface 712 enables bidirectional communication between the detection device 702 and the tablet computer 704 and/or smartphone 706. The communications interface 712 can enable wired or wireless communications.

For example, communications interface 712 can include the appropriate hardware and/or software to implement one or more of the following wired communication protocols such as Universal Serial Bus (USB), USB 2.0, IEEE 1394, Peripheral Component Interconnect (PCI), Ethernet, Gigabit Ethernet, and the like. The USB and USB 2.0 standards are described in publications such as Andrew S. Tanenbaum, Structured Computer Organization § 3.6.4 (5th ed. 2006); and Andrew S. Tanenbaum, Modern Operating Systems 32 (2d ed. 2001). The IEEE 1394 standard is described in Andrew S. Tanenbaum, Modern Operating Systems 32 (2d ed. 2001). The PCI standard is described in Andrew S. Tanenbaum, Modern Operating Systems 31 (2d ed. 2001); Andrew S. Tanenbaum, Structured Computer Organization 91, 183-89 (4th ed. 1999). The Ethernet and Gigabit Ethernet standards are discussed in Andrew S. Tanenbaum, Computer Networks 17, 65-68, 271-92 (4th ed. 2003).

In another example, communications interface 712 can include the appropriate hardware and/or software to implement one or more of the following proprietary wired communication protocols such as the 8-pin or 30-pin connectors utilized on various generations of iOS products such as IPHONE® smartphones and IPAD® table computers available from Apple Inc. of Cupertino, Calif.

In another example, communications interface 712 can include the appropriate hardware and/or software to implement one or more of the following wireless communication protocols: BLUETOOTH®, IEEE 802.11, IEEE 802.15.4, and the like. The BLUETOOTH® standard is discussed in Andrew S. Tanenbaum, Computer Networks 21, 310-17 (4th ed. 2003). The IEEE 802.11 standard is discussed in Andrew S. Tanenbaum, Computer Networks 292-302 (4th ed. 2003). The IEEE 802.15.4 standard is described in Yu-Kai Huang & Ai-Chan Pang, "A Comprehensive Study of Low-Power Operation in IEEE 802.15.4" in MSWiM'07 405-08 (2007).

Detection device 702 can be adapted and configured for mounting on tablet computer 704 or smartphone 706. Depending on the dimensions and mass of the detection device 702, detection device 702 can be supported solely by the connector (e.g., a USB, 8-pin, or 30-pin connector) or can receive additional support from one or more straps, bands, and the like that can serve to reduce stresses on the connector.

In another embodiment, detection device 702 is adapted and configured for connection to tablet computer 704 or smartphone 706 via one or more cords (e.g., a USB cord). In still another embodiment, detection device 702 is adapted and configured for connection to tablet computer 704 or smartphone 706 wirelessly. The latter two means of connection advantageously allow for the detection device 702 to be positioned remotely from tablet computer 704 or smartphone 706. Such flexibility allows, for example, for the detection device to be mounted within a screening cabinet that isolates the detection device 702 and the sample(s) from ambient light. In another embodiment, a first customs agent utilizing the detection device 702 can quickly move from sample to sample while a second customs agent views the data and/or analysis on the tablet computer 704 or smartphone 706.

By leveraging the components and capabilities of a tablet computer 704 or smartphone 706, various components can be omitted from the detection device 702 without impairing its performance. For example, a display screen 52 and many or all of push buttons 64, 60 can be omitted from the detection device 702, as color images can be displayed on and operation of the detection device 702 can controlled via the tablet computer 704 or smartphone 706. Use of a tablet computer 704 or smartphone 706 also allows for processing, storing, or e-mailing images/videos acquired by the detection device 702. Images and video can be stored in various formats such as SVG, JPEG, TIFF, RAW, PNG, GIF, BMP, BETAMAX®, BLU-RAY DISK®, DVD, D-VHS, Enhanced Versatile Disk (EVD), HD-DVD, Laserdisc, M-JPEG, MPEG-1, MPEG-2, MPEG-4, Ogg-Theora, VC-1, VHS, and the like. Additionally or alternatively, the intensity of emitted light at various wavelengths can be quantitatively measured and the numeric values presented and/or saved for analysis. For example, the numeric values can be saved in a comma-separated value (CSV) file or MICROSOFT® EXCEL® spreadsheet.

Detection device 702 can include a variety of components for imaging at various wavelengths. For example, the detection device 702 can include one or more charge-coupled devices (CCDs) 734 as discussed above. Illumination can be provided a plurality of light sources 728 such as LEDs and/or white/Tungsten light. In one embodiment, the detection device 702 can produce nine distinct wavelengths (e.g., 365 nm, 375 nm, 405 nm, 455 nm, 470 nm, 535 nm, 630 nm, 667 nm, 850 nm, and 1050 nm) in addition to white/Tungsten light. Additionally or alternatively, the detection device 702 can also emit energy at a wavelength of 575 nm (i.e., yellow), which can be utilized for crime scene investigations. Detection device can include a rotary or a linear filtering device as described in U.S. Pat. No. 5,245,179 to selectively apply one or more filters over CCDs 734.

Detection device 702 can be configured to automatically capture a plurality of images illuminated and/or filtered at a various frequencies. Such a device is advantageously much quicker and easier to use that devices that require a user to identify which frequencies may be of interest and then manually select appropriately illumination and/or filtering frequencies. In one embodiment, the detection device 702 captures one or more images at every possible setting (i.e., every combination of illumination and filtering frequency), compares the resulting data to a database of known signatures for valid products, and alerts the user if the signature is not valid. In another embodiment, the user selects the ostensible product and/or brand information for the product in question on the tablet computer 704 or smartphone 706 and the tablet computer 704 or smartphone 706 specifies one or more image settings that are relevant in assessing the propriety of the product in question.

In some embodiments, table computer 704 and/or smartphone 706 communicate periodically with a personal computer 742 and/or server 744 to updated images of and/or data pertaining to authentic and/or counterfeit products. In some embodiments, data is first downloaded from server 744 to personal computer 742 and the table computer 704 and/or smartphone 706 is then synced with the personal computer 742.

Electronic Control of LED Groups

Figure 8:
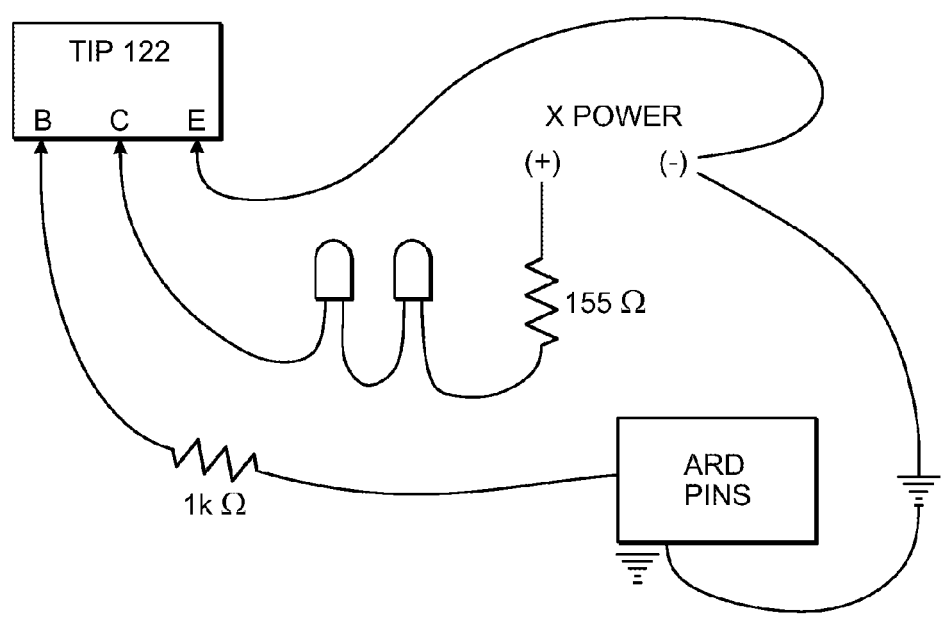
FIG. 8 depicts a low-voltage microprocessor configured to control relatively high voltage electronic components according to an embodiment of the present invention.

Referring now to FIG. 8, another aspect of the invention utilizes a relatively low-voltage microprocessor (e.g., an ARDUINO® microprocessor available from Arduinio, LLC of Cambridge, Mass.) to control relatively high voltage electronic components such as LEDs.

Instead of passing the relatively high voltage electricity through the microprocessor (which could damage or destroy the microprocessor), the microprocessor controls a transistor, which in turn, selectively completes a path from the LEDs to ground. Thus, the relatively high voltage does not pass through the microprocessor.

Exemplary Device Configurations

Figure 9:
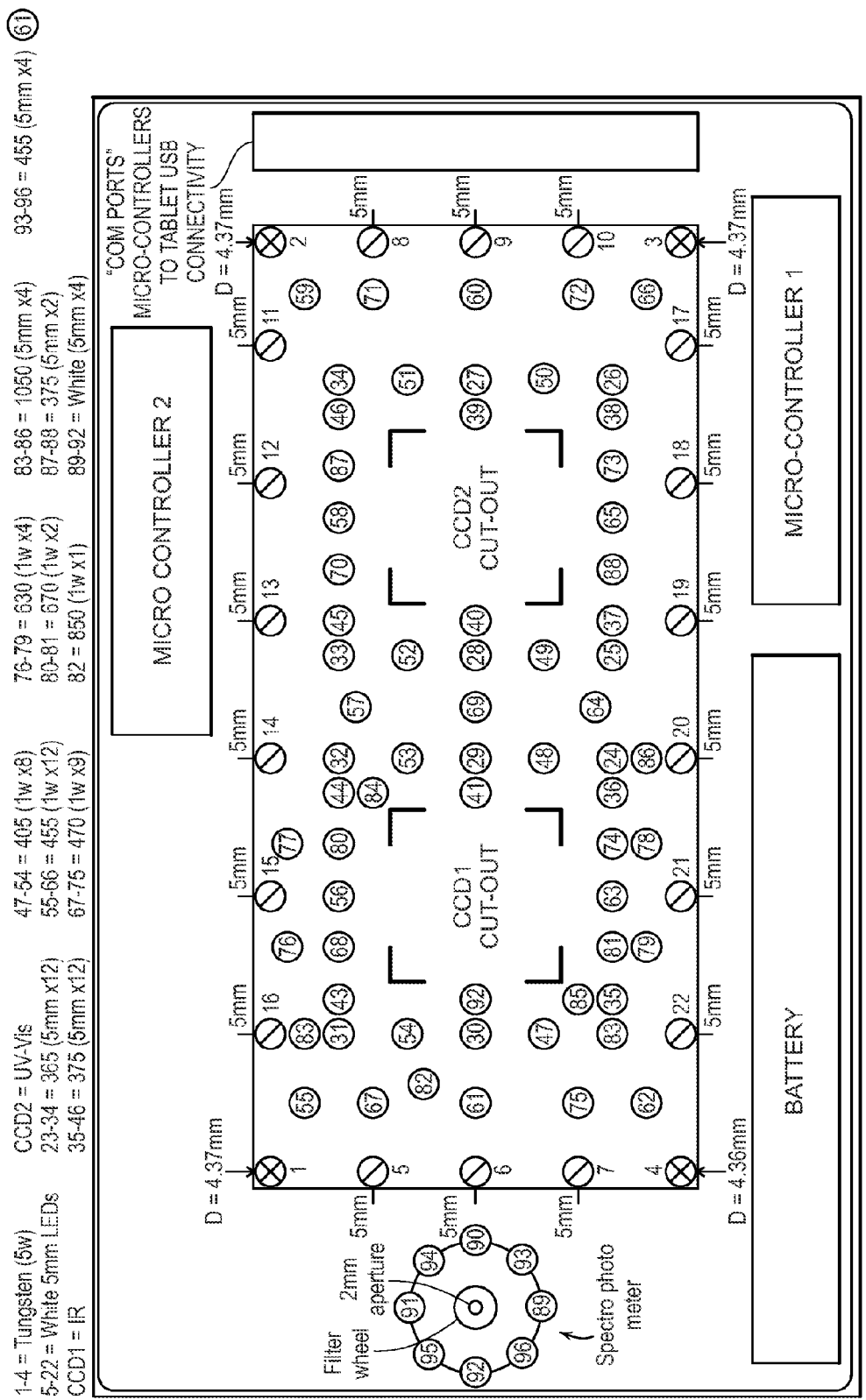
FIG. 9 depicts a bottom view of circuit board according to an embodiment of the invention.

Referring now to FIG. 9, a bottom view of circuit board according to an embodiment of the invention provided herein is depicted. The circuit board includes cut outs for two image acquisition devices (e.g., CCDs) and a number of LEDs. The circuit board can be in communication with one or more adjacent batteries, micro-controllers, communication ports, and or spectrophotometers. The emission frequencies of the LEDs are listed above the schematic.

Figure 10:
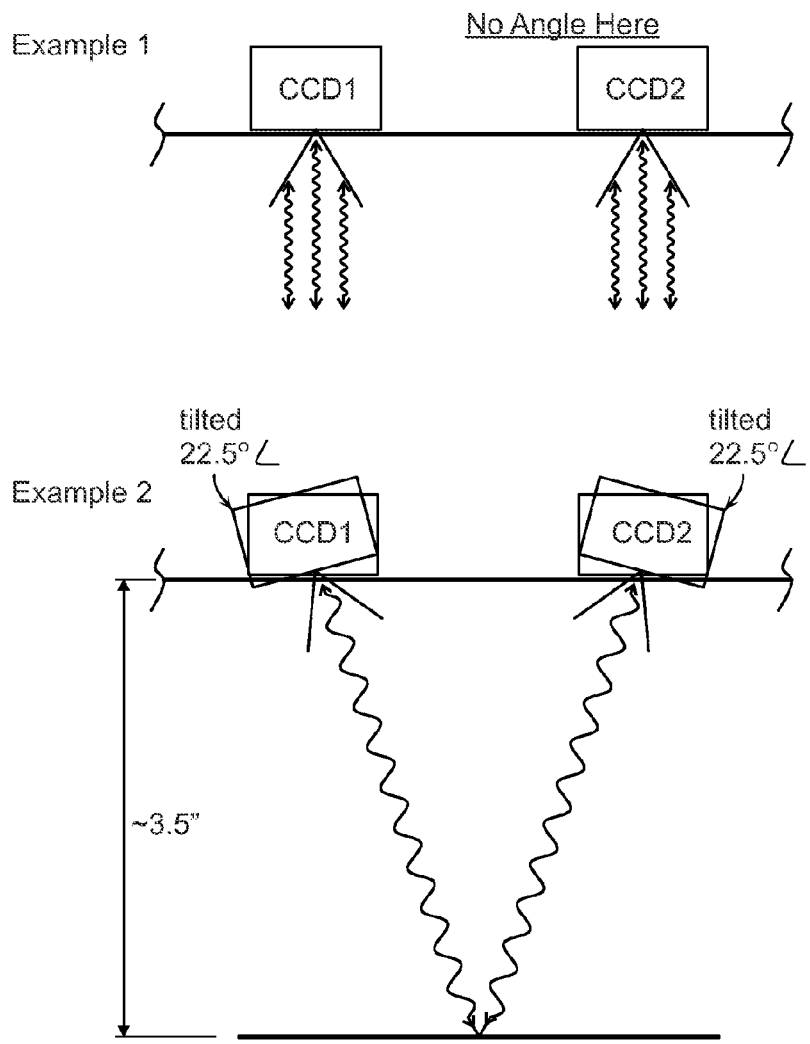
FIG. 10 depicts tilted image acquisition devices according to an embodiment of the invention.

Referring now to FIG. 10, some embodiments of the invention tilt image acquisition devices (e.g., CCDs) with respect to a plan defined by the bottom of the device and/or the LEDs. For example, the image acquisition devices can be tilted about 22.5° with respect to the bottom of the device.

Tilted image acquisition devices provide several advantages. First, a tilted image acquisition device will receive more reflected energy from the product of interest. Second, tilted image acquisition devices can be aimed at the same location within a focal plane, thereby facilitating simultaneous imaging of the same location at different frequencies.

Figure 11:
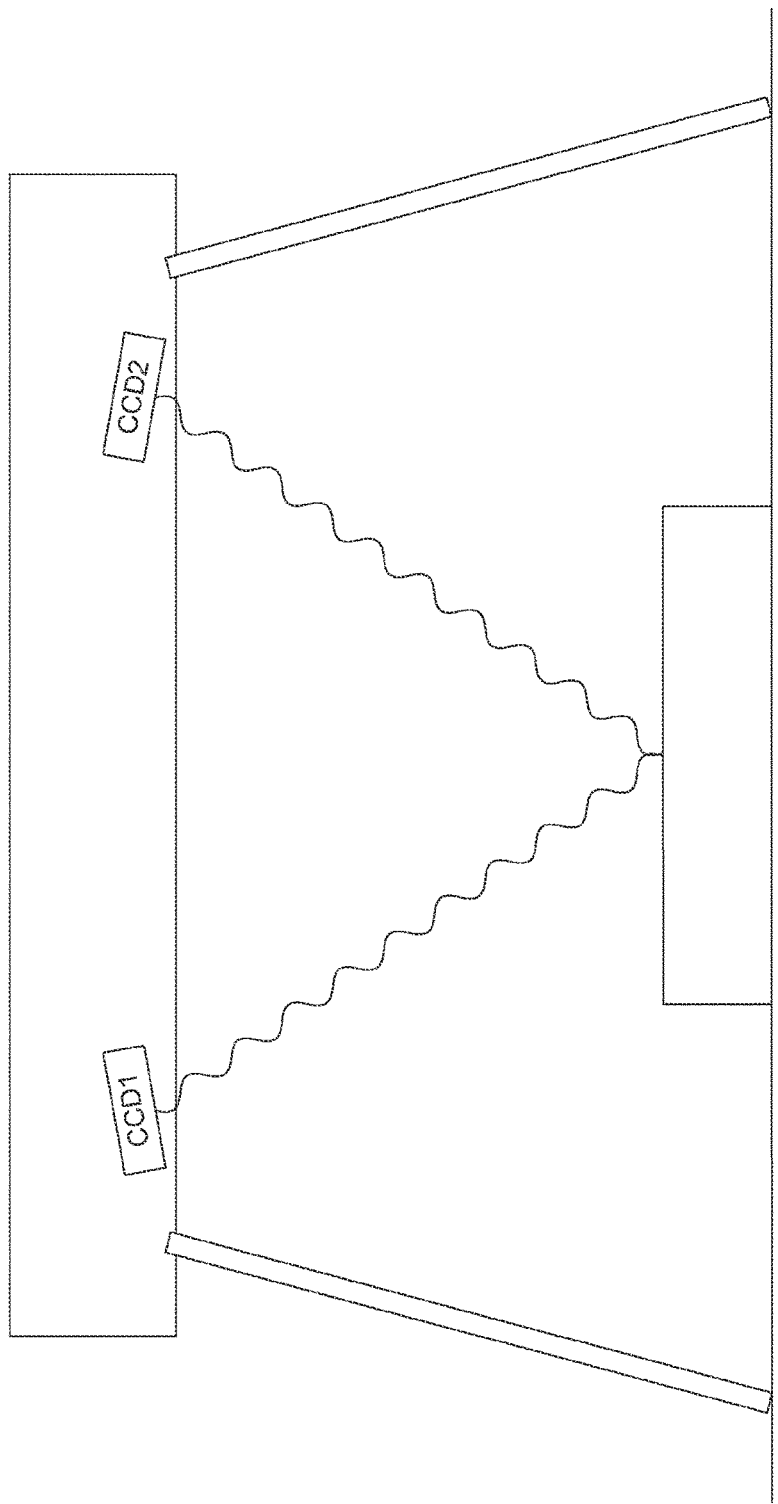
FIG. 11 depicts a device including a pair of legs that can be unfolded to allow the device to stand on a table, desk, counter, or other surface according to an embodiment of the invention.

An example of this focusing can be seen in FIG. 11, which depicts an embodiment of the device including a pair of legs that can be unfolded to allow the device to stand on a table, desk, counter, or other surface.

Figure 12:
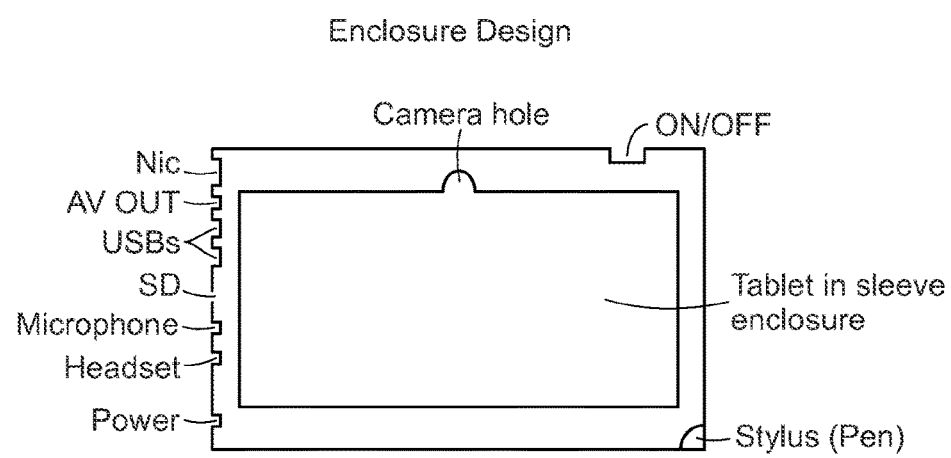
FIG. 12 depicts a top view of a device according to an embodiment of the invention.

Referring now to FIG. 12, a top view of an exemplary device is provided. This particular example shown is designed to interact with a WINDOWS® tablet computer, but the configuration can be easily modified to compliment any other tablet computer or smartphone.

Figure 13:
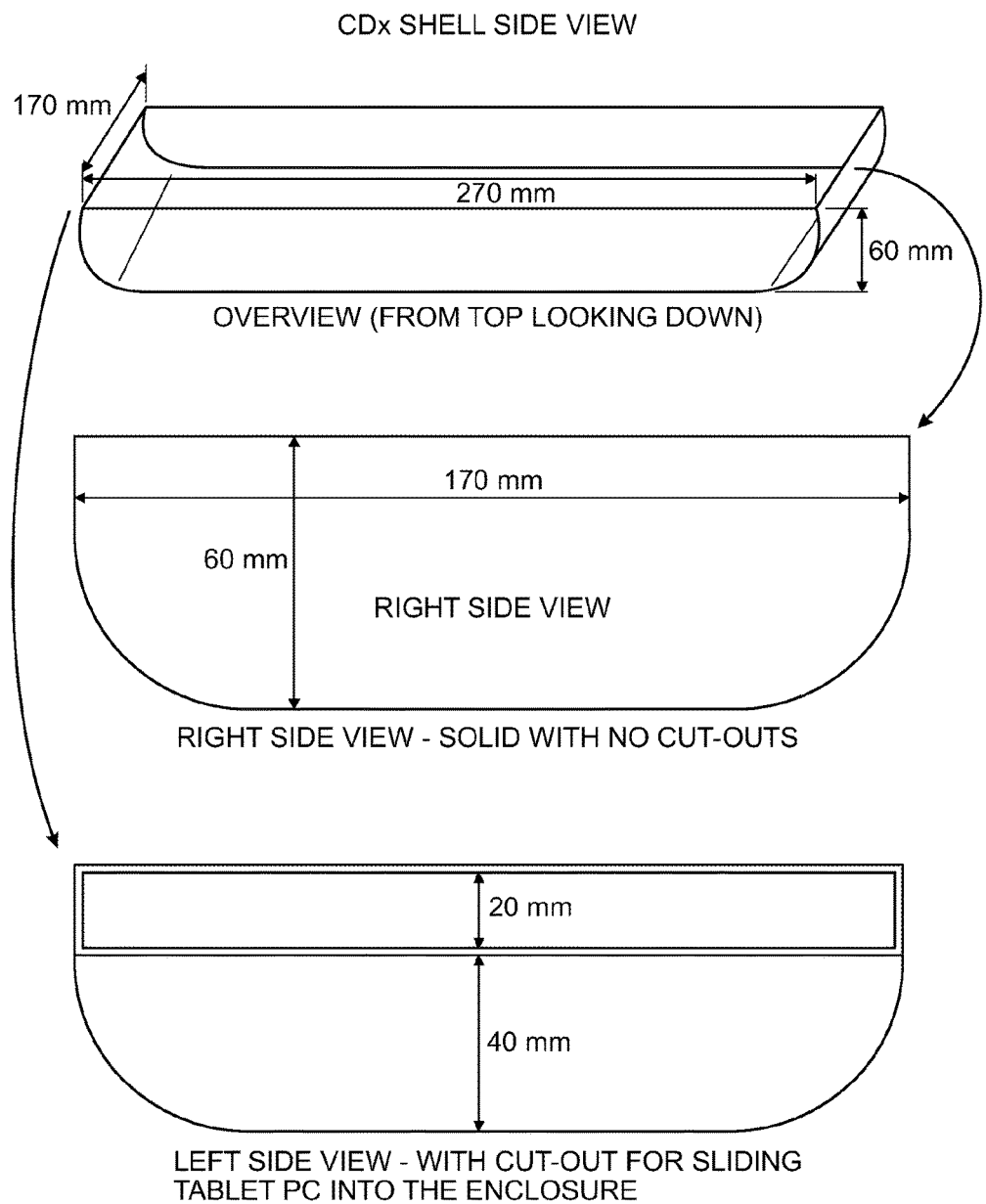
FIG. 13 depicts perspective, right side, and left side view of an device according to an embodiment of the invention.

Referring now to FIG. 13, perspective, right side, and left side view are of an exemplary device are provided. Notable, a tablet computer or smartphone can be received within the rectangular opening on the left side of the device.

Figure 14:
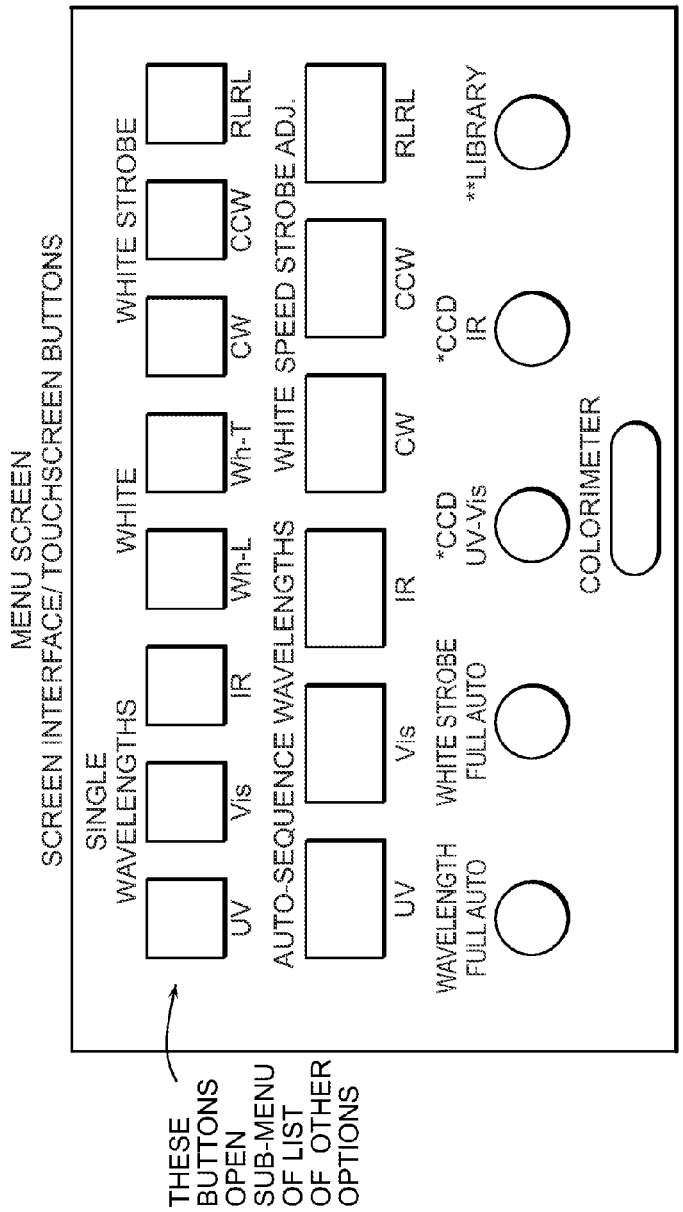
FIG. 14 depicts an exemplary graphical user interface (GUI) according to an embodiment of the invention.

Referring now to FIG. 14, an exemplary graphical user interface (GUI) is depicted. This GUI can be displayed on a display screen of the tablet computer or smartphone and/or can be displayed on a display screen integral to the device. Such a display screen can be programmed using a variety of platforms such as ADOBE® FLASH®, available from Adobe Systems Incorporated of San Jose, Calif.

INCORPORATION BY REFERENCE

All patents, published patent applications and other references disclosed herein are hereby expressly incorporated by reference in their entireties by reference.

EQUIVALENTS

Those skilled in the art will recognize, or be able to ascertain using no more than routine experimentation, many equivalents of the specific embodiments of the invention described herein. Such equivalents are intended to be encompassed by the following claims.

What is claimed is:

1. A device for detecting counterfeit pharmaceutical tablets or capsules, the device comprising:
    a plurality of light sources configured to emit light at a plurality of different wavelengths onto an illuminated pharmaceutical tablet or capsule;
    first and second image acquisition devices adapted and configured to acquire image data of the illuminated pharmaceutical tablet or capsule, wherein the image data comprises color or brightness of the pharmaceutical tablet or capsule;
    a communications interface adapted and configured to transmit the image data to a computing device selected from the group consisting of: a tablet computer and a smartphone;
    a housing including a lower surface, the plurality of light sources being coupled to the housing and arranged in the housing in a fixed relationship to the first and second image acquisition devices, the first and second image acquisition devices being tilted toward each other and aimed at a same location within a focal plane on the pharmaceutical tablet or capsule, wherein the first and second image acquisition devices are each tilted at about 22.5 degrees with respect to a plane defined by the lower surface of the housing;
    wherein operation of the plurality of light sources and the first and second image acquisition devices is configured to be controlled from a separate tablet computer or a smartphone via graphical user interfaces displayed on a display screen of the tablet computer or smartphone;
    wherein some of the plurality of light sources are configured to illuminate the pharmaceutical tablet or capsule by emitting light at different wavelengths from one another, wherein one or more of the different wavelengths produce a detectable difference in color or brightness of the image data of the pharmaceutical tablet or capsule that distinguishes between a counterfeit and authentic pharmaceutical tablet or capsule.

2. The device of claim 1, further comprising one or more filters adapted and configured to selectively filter selected wavelengths of light from entering the first and/or second image acquisition device wherein the selected wavelengths of light distinguish between a counterfeit and authentic pharmaceutical tablet or capsule.

3. The device of claim 2, wherein the plurality of light sources includes light sources that emit light having an infrared wavelength, visible wavelength, ultraviolet wavelength, or any combination thereof, and the device is configured to acquire one or more images at multiple combinations of illumination and filtered wavelengths.

4. The device of claim 1, wherein the first and second image acquisition devices are configured to simultaneously image the same location at the different wavelengths of light.

5. The device of claim 1, wherein the one or more wavelengths detect a difference in color between the counterfeit and authentic pharmaceutical tablet or capsule.

6. The device of claim 5, wherein the housing further comprises a plurality of foldable legs that when unfolded support the device at a predetermined height above a support surface on which the pharmaceutical tablet or capsule is placed to allow the first and second image acquisition devices to image the same location on the pharmaceutical tablet or capsule.

7. The device of claim 5, wherein the light sources comprise yellow light having a center frequency of 575 nm.

8. The device of claim 5, wherein the housing is configured to receive a tablet computer or a smartphone mounted within the housing.

9. A device for distinguishing between a counterfeit and authentic pharmaceutical tablet or capsule, the device comprising:
    a housing including a substantially flat lower surface;
    a plurality of different light sources coupled to the housing and being arranged in the flat lower surface of the housing, the different light sources emitting illumination light of different illumination wavelengths onto an illuminated object, wherein the object is a pharmaceutical tablet or capsule;
    first and second image acquisition devices coupled to the lower surface of the housing and tilted toward each other with respect to the lower surface of the housing to aim at a same location on the object, wherein the image acquisition devices are adapted and configured to acquire image data about the color of the illuminated object at the same location, and wherein the first and second image acquisition devices are each tilted at about 22.5 degrees with respect to a plane defined by the lower surface of the housing; and
    one or more filters that filter reflected light returning from the illuminated object to the image acquisition devices, wherein the different illumination wavelengths of the different light sources produce a detectable difference in image data about color between the counterfeit and authentic object when viewed through the one or more filters;
    a communications interface configured to:
        transmit image data from the first and second image acquisition devices to a computing device; and
        receive control signals from the computing device, the control signals including one or more image settings comprising illumination and filtering wavelength information related to assessing whether the illuminated object is authentic or counterfeit.

10. The device of claim 9 wherein the control signals illuminate
    the object with the device at an illumination wavelength with at least one of the plurality of light sources;
    filter reflected light of the illumination wavelength through the one or more filters as it is reflected from the illuminated object to the first and second image acquisition devices;

simultaneously acquire images with the first and second image acquisition devices from the same location on the object to produce image data of the object; and with the communications interface, transmit the image data for display on the computing device, the computing device comprising a tablet computer or a smartphone, for identifying any difference in color of the object that would distinguish a counterfeit pharmaceutical tablet or capsule.

11. The device of claim 10, wherein the control signals illuminate the object sequentially at different wavelengths of light from different of the light sources and filter the returning light with multiple different of the filters.

12. The device of claim 10, wherein the computing device compares the image data of the illuminated object obtained from the first and second image acquisition devices to image data of an authentic product in a database storing image data of known authentic products to determine whether the illuminated object is an authentic product.

13. The device of claim 1 wherein the computing device compares the image data of the illuminated object to image data of an authentic product in a database of stored image data of known authentic products to determine whether the object is an authentic product.

14. The device of claim 10, wherein the detectable difference in image data about color of the object are produced by differences in one or more components within the pharmaceutical tablet or capsule.

15. The device of claim 14, wherein the component within the pharmaceutical product comprises an excipient within the pharmaceutical tablet or capsule that produces the detectable difference in color or brightness.

16. The device of claim 1, wherein the detectable difference in color or brightness of the image data is produced by differences in one or more components within the pharmaceutical tablet or capsule.

17. The device of claim 16, wherein the component within the pharmaceutical product comprises an excipient within the pharmaceutical table or capsule that produces the detectable difference in color or brightness.

\* \* \* \* \*